(12) United States Patent
Tomkins et al.

(10) Patent No.: US 6,382,522 B2
(45) Date of Patent: *May 7, 2002

(54) ATTACHMENT METHOD FOR PIEZOELECTRIC ELEMENTS

(75) Inventors: David A. Tomkins, Racine, WI (US); George A. Clark, Lewis Center; Eric R. Navin, Delaware, both of OH (US); Edward J. Martens, III, Racine, WI (US)

(73) Assignee: S. C. Johnson & Son, Inc., Racine, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/518,882

(22) Filed: Mar. 6, 2000

Related U.S. Application Data

(60) Provisional application No. 60/123,208, filed on Mar. 8, 1999.

(51) Int. Cl.[7] .............................. B05B 1/08; B05B 3/04; B05B 17/04
(52) U.S. Cl. ................. 239/102.2; 239/102.1; 239/4
(58) Field of Search .......................... 239/102.1, 102.2, 239/4; 346/140.1, 141; 347/6, 9, 20, 47, 68, 70

(56) References Cited

U.S. PATENT DOCUMENTS

| | | | | | |
|---|---|---|---|---|---|
| 4,295,373 A | * | 10/1981 | Moffatt | ......................... | 73/505 |
| 4,305,293 A | * | 12/1981 | Swarts | ......................... | 73/505 |
| 4,308,546 A | | 12/1981 | Halasz | .................... | 346/140 R |
| 4,564,297 A | * | 1/1986 | Firth | ........................... | 366/108 |
| 5,208,506 A | * | 5/1993 | Yamashita | ................... | 310/328 |
| 5,325,012 A | * | 6/1994 | Sato et al. | ................... | 310/364 |
| 5,881,714 A | * | 3/1999 | Yokoi et al. | ........... | 128/200.14 |
| 5,938,117 A | | 8/1999 | Ivri | ................................ | 239/4 |

* cited by examiner

Primary Examiner—Henry C. Yuen
Assistant Examiner—Davis Hwu

(57) ABSTRACT

Disclosed herein is a piezoelectric liquid delivery system or atomizer for production of droplets of liquid or liquid suspensions by means of a battery operated atomizer utilizing an orifice plate in communication with a ceramic piezoelectric element. By use of solder joining to bond the orifice plate to the piezoelectric element, and subsequent repolarization of the piezoelectric element if necessary, superior results are achieved.

3 Claims, 5 Drawing Sheets

ATTACHMENT METHOD FOR PIEZOELECTRIC ELEMENTS

PRIORITY

This application claims the benefit of U.S. Provisional Application No. 60/123,208, filed Mar. 8, 1999.

TECHNICAL FIELD

The present invention relates, broadly, to the field of atomization of liquids for dispersal in the form of aerosols. More specifically, the invention relates to means for the distribution of a liquid active material, such as a perfume, air freshener, insecticide formulation, or other material, in the form of fine particles or droplets, as in a fine spray, by means of a piezoelectric device. In particular, the invention is directed to a piezoelectric liquid delivery system for the production of droplets of liquid, or liquid suspensions, by means of an electomechanical or electroacoustical actuator. More specifically, the present invention relates to a battery operated piezoelectric dispenser utilizing an orifice plate in communication with a piezoelectric element. It has been found that by joining the orifice plate to the vibrating piezoelectric element by a soldering method, rather than the conventional adhesive or bonding techniques, performance degradation of the piezoelectric atomization, i.e. a decline in release rate, is avoided. This is of particular value in the atomization of perfumes and fragrance oils, which attack the normal adhesives, especially under high rates of flexing or vibration.

BACKGROUND ART

The distribution of liquids by formation of a fine spray, or atomization, is well known. One method for such distribution is to atomize a liquid by means of the acoustic vibration generated by an ultrasonic piezoelectric vibrator. An example of such a method is shown in Carter, U.S. Pat. No. 4,702,418, which discloses an aerosol dispenser including a nozzle chamber for holding fluid to be dispensed, and a diaphragm forming at least a portion of the chamber. An aerosol dispensing nozzle is disposed therein, with a restrictive passage for introducing fluid from the reservoir to the nozzle. A pulse generator in combination with a low voltage power source is used to drive a piezoelectric bender, which drives fluid from the reservoir through the nozzle to create an aerosol spray.

Another atomizer spraying device is shown by Humberstone et al, in U.S. Pat. No. 5,518,179, which teaches a fluid droplet production apparatus comprising a membrane which is vibrated by an actuator which has a composite thin-walled structure, and is arranged to operate in a bending mode. Fluid is supplied directly to a surface of the membrane and sprayed therefrom in fine droplets upon vibration of the membrane.

U.S. Pat. No. 5,297,734 of Toda teaches ultrasonic atomizing devices comprising piezoelectric vibrators with a vibrating plate connected thereto, by means of a conductive adhesive. In this patent, the vibrating plate is described as having a large number of minute holes therein for passage of the fluid.

Ivri et al, in U.S. Pat. No. 5,586,550, teach apparatus for the delivery of therapeutic liquids, including a vibratable non-planar member having tapered apertures, to which liquid is delivered by squeezing a liquid reservoir to deposit it directly on the surface, in such a manner that all of the liquid adheres to the vibratable member by surface tension. The piezoelectric element is bonded to a vibratory cantilever beam to provide oscillation to a carrier plate and thin shell non-planar member so as to nebulize the liquid in contact therewith.

U.S. Pat. No. 4,479,609, of Maeda et al, discloses a liquid sprayer comprising an ultrasonic vibrator, a liquid supply chamber, and a liquid absorber for transporting liquid from the chamber to the vibrator. The electrostrictive element is connected to the metallic horn by a conductive adhesive. Further, in U.S. Pat. No. 4,533,082, Machara et al teach an arrangement for discharging liquid droplets, wherein a piezoelectric transducer is secured to a vibrating member to induce a displacement of the liquid through a nozzle opening. An axially vibrating disc is cemented to a ring shaped piezoelectric transducer of polarized ceramic. The disclosures of these patents, and of all other publications referred to herein, are incorporated by reference as if fully set forth herein.

Such atomizers and/or dispensers fail to provide a system by which liquid to be dispersed is supplied to the vibratory mechanism/surface without resulting in corrosion, solvent activity by the active liquid, or bond failure at the point of joining of the piezoelectric element and the orifice plate, particularly when the active liquids are such as perfumes or insecticides, having high activity quotients at high rates of vibration. Moreover, the prior art has failed to provide an easily portable, battery operated, continuous-action dispenser employing an orifice plate in soldered connection with a ceramic piezoelectric element, capable of long periods of use with little or no variation in the delivery rate. Thus, a need exists for an improved method for joining piezoelectric transducers to orifice plates or other elements of a piezoelectric atomizer.

DISCLOSURE OF INVENTION

It is an object of the present invention to provide a highly efficient, consistent, and reliable dispenser for liquid active materials, employing an orifice plate securely joined with a ceramic piezoelectric element. While the invention is described as comprising a ceramic piezoelectric element, it is understood that the invention is not limited thereto, but also extends to other piezoelectric materials having the requisite properties for use, and resistance to the elevated temperatures which accompany joining elements by soldering. By liquid active materials, it is meant to include such liquids as perfumes, air fresheners, household cleaning materials, disinfectants, repellants, insecticides, aroma therapy formulations, medicinals, therapeutic liquids, or other liquids or liquid suspensions which benefit from atomization for use. These compositions may be aqueous, or comprise various solvents. In a preferred embodiment of the invention, the piezoelectric liquid delivery system is easily portable, battery operated, and conveniently refillable with the same, or a different, liquid active It is a further object to provide a piezoelectric pump capable of operating efficiently for months, on low voltage batteries, while maintaining consistency of delivery throughout the period. Included in such object is to provide a piezoelectric atomizer suitable for use with such electrical sources as 9 volt batteries, conventional dry cells such as "A", "AA", "AAA", "C", and "D" cells, button cells, watch batteries, and solar cells or solar power. The preferred energy sources for utilization in combination with the present invention are "AA" and "AAA" cells.

In still another object, it is desired to provide a liquid delivery system capable of atomizing fragrance oil or insecticide formulation linearly over time, while maintaining the same character/composition on the last day as was delivered on the first, i.e. with no component change or separation with time. The electronics of such a unit may preferably be programmable, and may be used to set a precise delivery rate (e.g. in milligrams per hour, or mg/hr), or may allow the consumer to adjust intensity or effectiveness to a desired level for personal preference, efficacy, or for room size.

Another object of this invention is to provide small droplets of pure fragrance or insecticide formulation which are propelled intermittently from the unit to form a small "cloud" or "puff," which droplets quickly diffuse and move throughout a large area on air currents present in said area. It is found that the small size of such droplets, and the correspondingly large ratio of surface area to mass, result in these droplets evaporating quickly and uniformly. In preferred embodiments, the delivery system operates with a linear delivery rate for several months on a single 1.5 volt "AA" size battery, delivering uniform volumes of essentially equally sized droplets of the liquid for the entire period.

These and other objects of this invention are achieved by a piezoelectric dispenser for fragrances, insecticide formulations, and other highly active liquids, wherein the dispenser includes a chamber for the liquid to be dispensed, means to supply the liquid from said chamber to an orifice plate for dispersal of the liquid, and a ceramic piezoelectric element, wherein the piezoelectric element is joined to the orifice plate by soldering, to achieve a bond which is superior to conventional adhesive bonding.

The fragrance or insecticide formulation is supplied to the back side of the orifice plate through a capillary feed system that delivers the liquid in surface tension contact with the plate, without damping the vibrational frequency to which the plate is subjected by the piezoelectric element. The piezoelectric element is driven by a small battery, capable of exciting the element and causing it to force liquid through the orifice plate, which has a multitude of small tapered or conical holes therein perpendicular to the surfaces thereof, the exit of said holes being on the order of 6 microns in diameter. Timing circuitry is used to provide an intermittent excitation to the piezoelectric element so as to dispense small droplets of said liquid in a time dependent fashion. Due to the nature of the liquids being atomized, i.e. the presence of organic components or solvents in the fragrance oils and/or insecticide formulations, it was found that conventional bonding methods for joining the orifice plate to the metallic cantilever beam of a conventional piezoelectric driver were inadequate. Conventional bonding agent exhibit significant degradation over time when in contact with fragrance oils, with the degradation believed to be accelerated by the flexing forces caused by the piezoelectric vibration. A soldering process was developed to eliminate this problem, using a lead/tin solder. In addition, it was found that the orifice plate could be attached directly to a piezoelectric ceramic element, eliminating the need for an extra part such as a cantilever beam or metal amplifying plate.

These and still other objects and advantages of the present invention will be apparent from the description which follows, which is, however, merely of the preferred embodiments. Thus, the claims should be looked to in order to understand the full scope of the invention.

MODES FOR CARRYING OUT THE INVENTION

Figure 5:
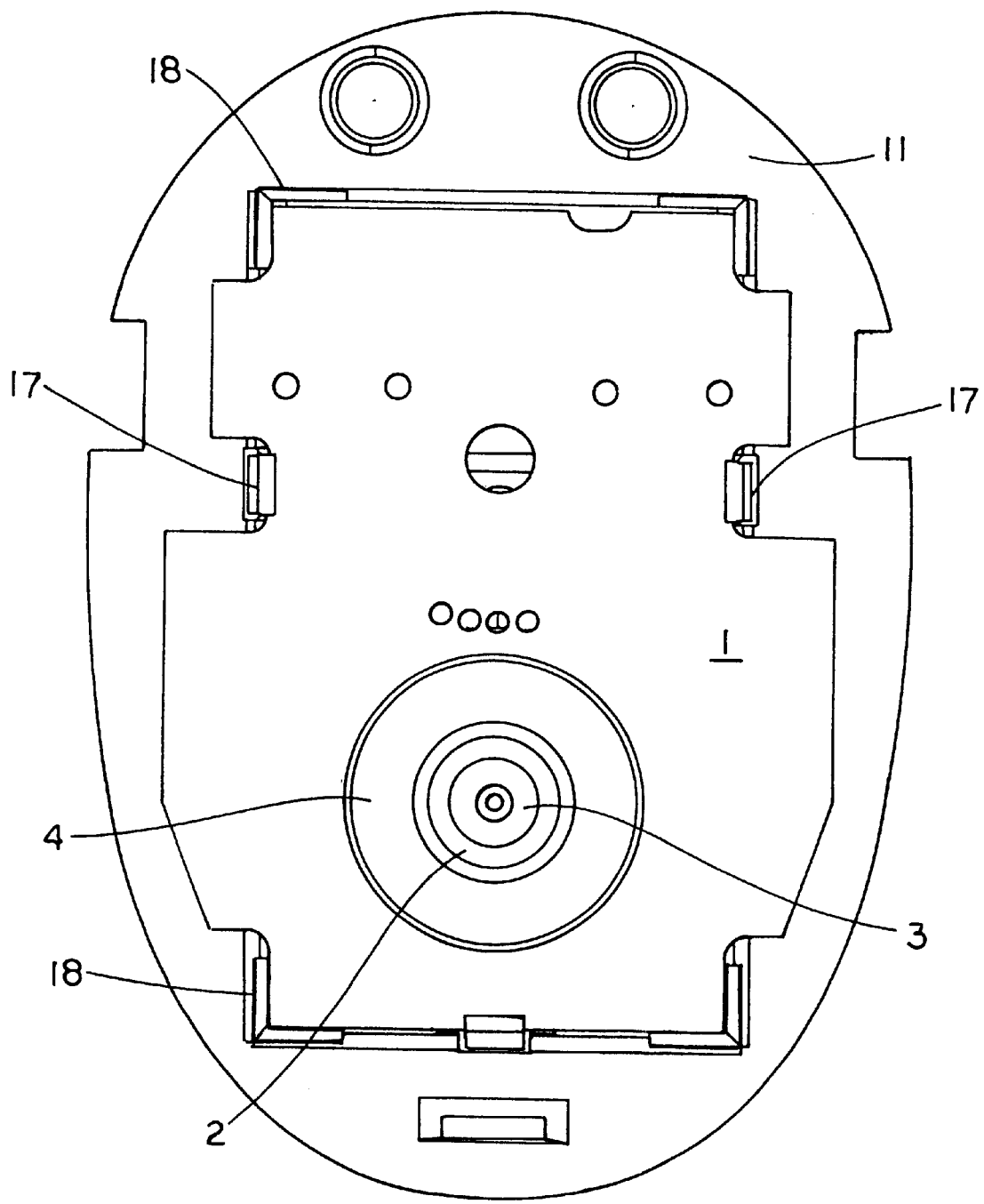
FIG. 5 is a top view of the piezoelectric element and the printed circuit board mounted on the chassis of a preferred embodiment
Figure 6:
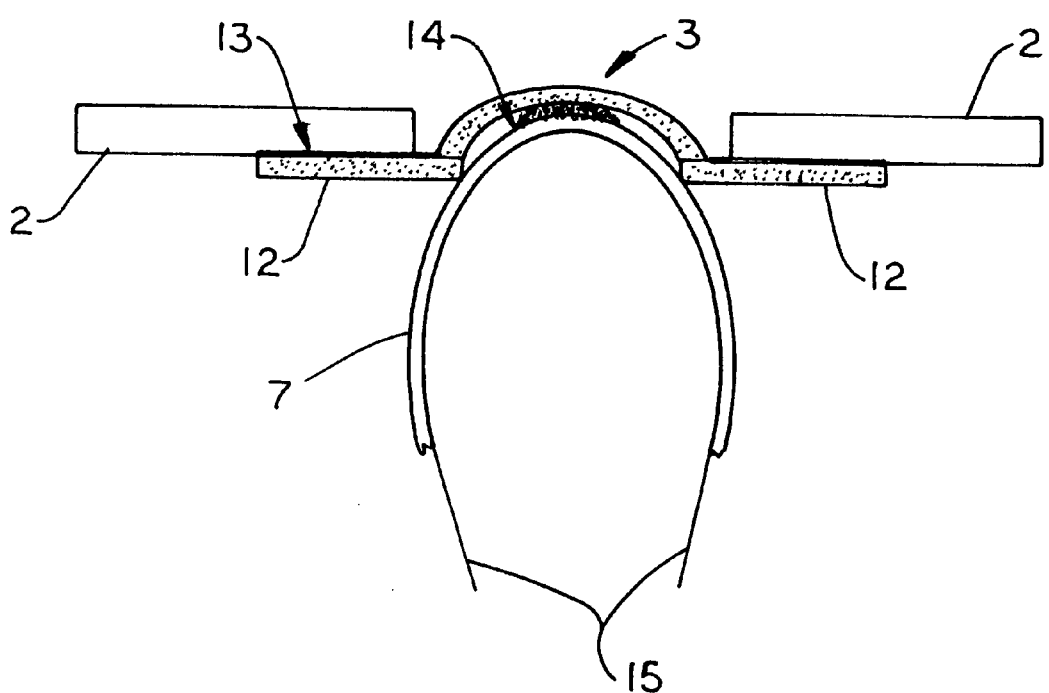
FIG. 6 illustrates a much simplified cross-sectional diagram of a piezoelectric pump assembly suitable for use with a preferred embodiment of the present invention.
Figure 7:
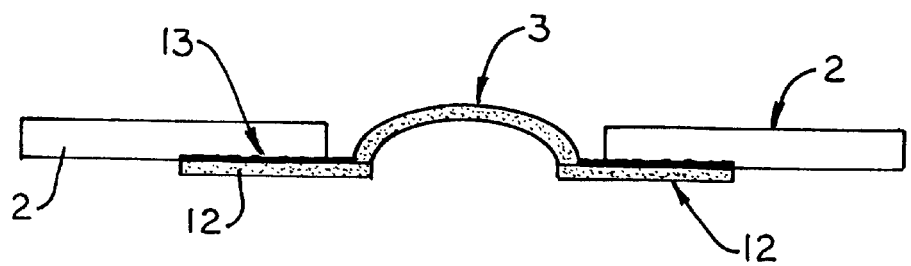
FIG. 7 illustrates a partial view, in detail, of a portion of FIG. 6, showing the domed orifice plate in communication with a ceramic piezoelectric element, the two elements being joined by a solder joint in accord with the present invention.
Figure 8:
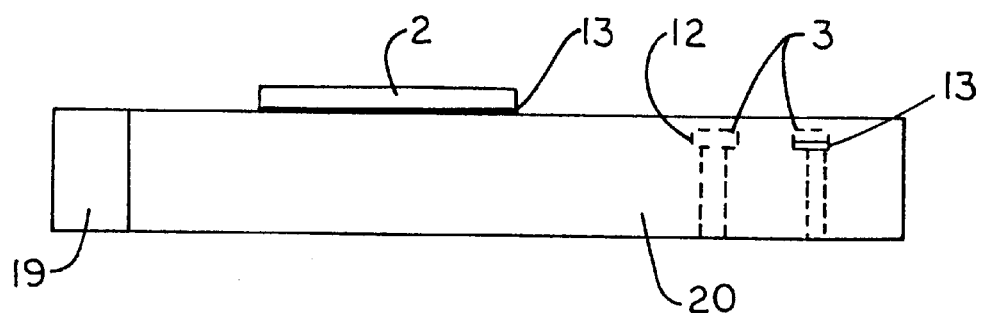
FIG. 8 illustrates a side view of a cantilever bar type of piezoelectric dispenser assembly.

While FIGS. 1 through 6 are more specifically directed to a preferred embodiment of the invention, FIGS. 7 and 8 are more generally directed to the full scope of the present invention, which envisions joining of the piezoelectric element to the orifice plate in a manner which is in contrast to the conventional practice of those of ordinary skill in the art.

Figure 1:
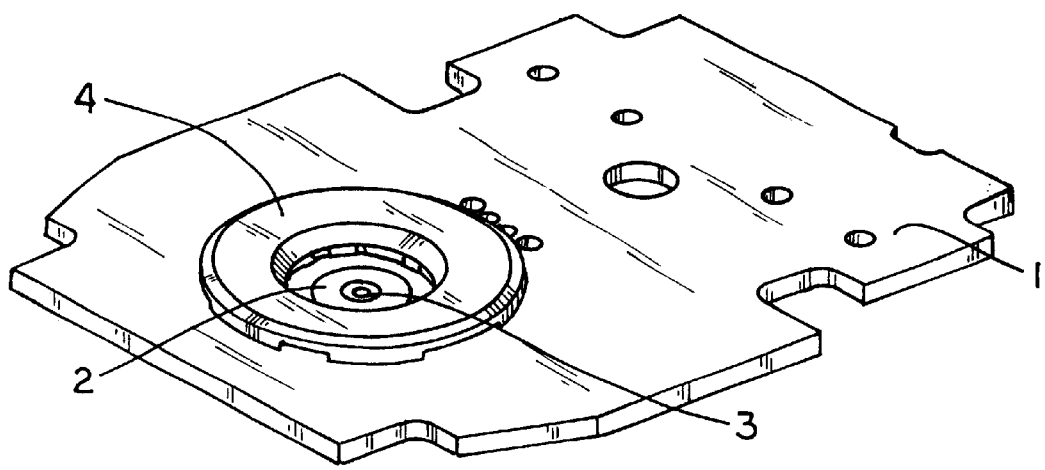
FIG. 1 is a partial isometric view of a circuit board suitable for use in a piezoelectric atomizer in accordance with a preferred embodiment of the present invention.

FIG. 1 illustrates the general relationship between a printed circuit board, 1, in which the piezoelectric element 2 is located. The circuit board, 1, is illustrated without the electronic circuitry and battery associated therewith for clarity and ease of understanding of the present invention. It is also to be understood that the circuit board is, in use, attached to the chassis of a dispenser, which chassis is in turn placed in a decorative shell-like housing or receptacle (not shown) for use. The chassis board 11 is shown in top view in FIG. 5, while the housing is not illustrated. The decorative receptacle or housing may be of any form or shape suitable for the purpose of retaining the elements of the dispenser while providing a pleasing appearance to the consumer, and permitting passage of the liquid, in spray form, from the dispenser to the atmosphere. As such, the dispenser housing may be advantageously produced by high speed molding of any material suitable for use with, and contact with, the liquid to be dispensed.

Piezoelectric element 2 may be mounted in the circuit board 1, held in place by grommet 4, or by any similar suitable means which does not inhibit vibration of the piezoelectric element. The piezoelectric element 2, in the form of a ring, is positioned in a concentric relationship to the orifice plate 3, and is attached to the orifice plate flange so as to be in vibratory communication therewith. The ceramic piezoelectric element generally comprises a piezoelectric ceramic material, such as a lead zirconate (PZT) or lead metaniobate (PN), but may be of any material exhibiting piezoelectric properties. The ceramic piezoelectric element is joined to the orifice plate in the manner set forth hereinafter.

The orifice plate comprises any conventional material suitable for the purpose, but may preferably be comprised of an electroplated nickel cobalt composition formed upon a photoresist substrate which is subsequently removed in conventional manner to leave a uniform porous structure of nickel cobalt having a thickness of from about 10 to about 100 microns, preferably from about 20 to about 80 microns, and most preferably about 50 microns. Other suitable materials for the orifice plate may be utilized, such as nickel, magnesium-zirconium alloy, various other metals, metal alloy, composites, or plastics, as well as combinations thereof. Other suitable materials may be used, having the appropriate grain size and wetting properties. By forming the nickel cobalt layer through electroplating, a porous structure having the contour of the photoresist substrate may be produced, in which permeability is achieved by formation of conical holes having a diameter of about 6 microns on the exit side, and a larger diameter on the entrance side. The orifice plate may be planar, but is preferably dome shaped, i.e. somewhat elevated at the center, and may vary from flat to parabolic, arc shaped, or hemispherical in shape. The plate should have a relatively high bending stiffness, to assure that the apertures therein shall be subject to the same amplitude of vibration, so as to simultaneously eject droplets of liquid which are uniform in diameter. The orifice plate may also be plated with such materials as gold, silver, and platinum for corrosion protection if desired.

Figure 2:
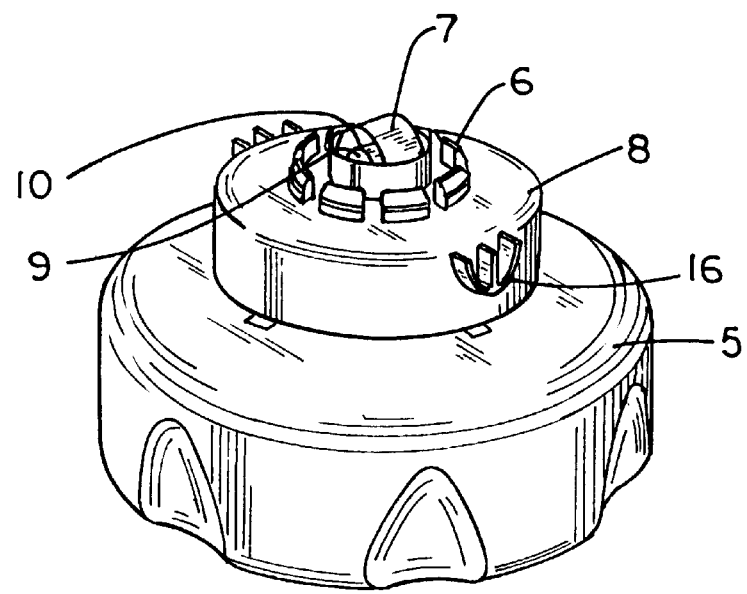
FIG. 2 is an isometric view of a liquid container and liquid transport means suitable to bring the liquid to the surface of the orifice plate.

Shown in FIG. 2 is the liquid container 5 for storage and provision of the fragrance, air freshener, insect control liquid, or other material to be dispensed. As illustrated, the container is closed by a removable closure 8, preferably a clip-on or screw-on closure. Also shown are bayonet clips 6, which are present to hold a removable top closure, or cap, not shown, which is used in transport and storage of the container, and may be removed easily when it is desired to put the container into the dispenser and permit use of the contents thereof. From bottle opening 9, exiting through the closure 8, projects the liquid supply means 7, a loop shaped wick or dome shaped liquid feed medium. For convenience, we shall refer to the liquid supply means as a wick, although it may comprise a number of varying shapes and materials, from hard plastic capillary systems to soft porous wicks. The function of the wick is to transport liquid from container 5 to a position in contact with the orifice plate. Accordingly, the wick should be unaffected by the liquid being transported, porous, and permit compliance with the orifice plate. The porosity of the wick should be sufficient to provide a uniform flow of liquid throughout the range of flexibility of the wick, and in any configuration thereof. To best transport the liquid to the surface of the orifice plate, it has been found necessary that the wick itself physically contact the plate, to transfer the liquid to the plate. Liquid is preferably delivered to the orifice plate in such a manner that essentially all delivered liquid will adhere to and transfer to the plate surface by surface tension. Among suitable wick materials, we have found it preferable to utilize such materials as paper, such as filter paper, or fabrics of cotton, nylon, polypropylene, fiber glass, etc. It is preferred that the wick comprise a highly porous material, having porosity and softness similar to a filter paper or tissue. A preferred wick material comprises a woven 100 percent cotton fabric, supplied by Spring Industries as a broadcloth weave having a 68 by 68 thread count, and a density of about 7.2 grams per 100 square inches. The preferred loop or wick utilized is preferably 0.125 inches wide, 2.75 inches long, and 0.01 inches thick. The preferred loop height, above the wick holder, is preferably from about 0.05 to about 0.15 inches, although loop height is dependent upon design of the liquid container, wick holder, and atomizer. The wick may preferably be shaped to conform to the surface of the orifice plate to which it is juxtaposed, and held in the correct position by a wick holder or positioner, 10, located in the bottle opening 9, of the closure 8 of liquid container 5. Liquid will flow readily from the wick to the plate as a result of the viscosity and surface tension of the liquid. It is to be noted that the wick is intended to be included as an integral part of a liquid resupply unit, which will comprise the container, the liquid, the bottle closure, the wick, and the wick holder or positioner, as well as a top closure to seal the unit for storage and shipment. Such a unit may thus comprise a refill bottle for the dispenser, suitable to be placed in the dispenser at the consumers convenience. To this end, the liquid container 5 may have attachment means 16 on the bottle closure 8, for insertion into a suitable receiving means in the chassis 11 to lock it in operative position, after removal of the top closure or cap. However, it is possible for the wick to be provided as an integral part of the orifice plate, the chassis, or another part of the atomizer, with means provided, such as wick tails, to bring the liquid in the liquid container into contact with the wick.

Figure 3:
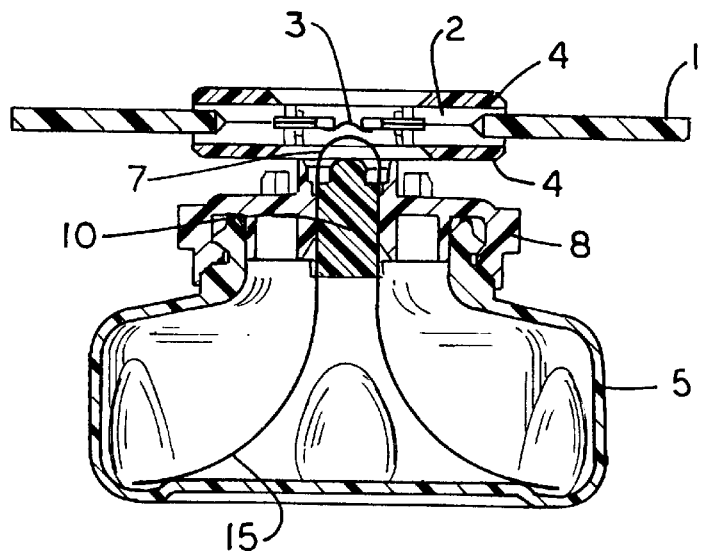
FIG. 3 is a cross sectional view showing the relationship of the liquid container, the feed means, and the piezoelectric element.
Figure 4:
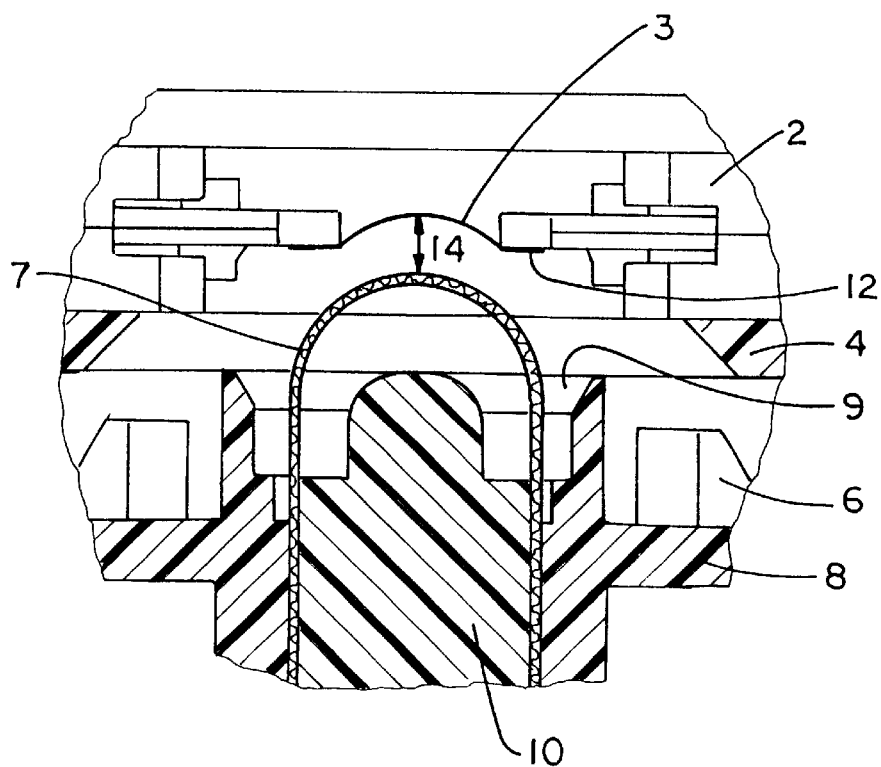
FIG. 4 is a magnified detail of the area of FIG. 3 enclosed within the circle shown in FIG. 3.

FIG. 3 illustrates, in cross sectional view, the relationship between the liquid container 5, the wick 7, the piezoelectric element 2, and the orifice plate 3 of a specific preferred embodiment of the invention. The piezoelectric element 2 is positioned, for example, in printed circuit board 1, by grommets 4, or by any suitable means which do not restrict vibration of the piezoelectric element. In a preferred embodiment, the annular piezoelectric element surrounds the orifice plate 3, in mechanical connection therewith. The orifice plate is, in turn, in juxtapostion with the wick 7, permitting flow of the liquid to be dispensed from the container 5 to the orifice plate, where transfer occurs through surface tension contact. Not shown is the chassis board 11 of the dispenser, which holds the circuit board 1 and the liquid container in the appropriate position to bring wick 7 into juxtaposition with the orifice plate 3. Wick 7 is held in the opening of closure 8 by the wick holder 10, which permits a degree of freedom to the flexible and highly compliant wick 7, so as to allow a range of adjustment thereof, while wick tail 15 assures complete utilization of all the liquid in the container 5. This degree of freedom permits self-adjustment of the wick relative to the surface of the orifice plate, to compensate for variations in position resulting from the vagaries of manufacture and shipment, and provides for a compliant feed means for transfer of the liquid from the container to the face of the orifice plate. As will be apparent to one skilled in the art, the height of the wick, as shown in FIGS. 3 and 4, may be adjusted to vary the liquid gap 14, as shown in FIGS. 4 and 6, and to assure an appropriate degree of contact between the wick and the plate. For a more detailed view of the relationship between the wick and the orifice plate, attention is directed to FIG. 4, a magnified detail of the circled section of FIG. 3, wherein is shown the looped wick 7, in juxtapostion with domed orifice plate 3, in which the liquid to be transferred is in surface tension contact with the orifice plate. While FIG. 4 shows the wick and the plate as in substantial contact throughout the full arc of the dome of the orifice plate, it is to be understood that this is for illustration only, and that plate 3 may in fact contact wick 7 for only a limited arc, as shown in FIG. 6, to achieve transfer of the liquid, dependent upon viscosity, surface tension, and temperature of the liquid, as well as the specific porosity and flexibility of the wick, and the extent of liquid gap 14. As shown, the passage of the wick 7 through the opening 9 in the closure element 8 is controlled by the wick holder/positioner 10. FIG. 4 also shows the mounting grommet 4 for the ceramic piezoelectric element 2, orifice plate 3, and the orifice plate flange 12, as well as the clips 6 which hold the removable cap (not shown) to the bottle closure 8.

FIG. 5 is a top view, showing the relationship of circuit board 1, piezoelectric element 2, orifice plate 3, mounting grommet 4, and the chassis board 11, of a preferred embodiment of the invention. As previously indicated, the piezoelectric element 2, in concentric relationship to the orifice plate 3, is held in place in the circuit board 1 by the grommet 4. The circuit board is mounted on chassis board 11 in conventional manner, such as with clips 17 and positioning brackets 18.

In FIG. 6, a simplified cross sectional diagram of a preferred embodiment of the invention illustrates the overall relationship of various elements. The orifice plate 3 is shown as including orifice plate flanges 12, which are in turn attached to the piezoelectric element 2 in accordance with the present invention. The wick 7 is illustrated in contact with the orifice plate 3, creating liquid gap 14, in which the liquid to be dispensed is transferred to the orifice plate. The wick is shown as also comprising fabric tails 15, which extend into the liquid container 5, not shown.

FIG. 7 illustrates the piezoelectric element and orifice plate assembly of FIG. 6, wherein the ceramic piezoelectric element, 2, surrounds the domed orifice plate 3, and is joined to the orifice plate by soldering the orifice plate flange 12 to the ceramic piezoelectric element at attachment points 13. In contrast to conventional practice, we have found that this attachment means is most appropriately a solder joint, rather than the usual adhesive means. To achieve a successful solder joint, it is appropriate to metallize the ceramic element to provide a base for the solder to adhere to. It is noted that the conventional wisdom teaches away from such a procedure, because this would require heating the ceramic piezoelectric element to a temperature at which depolarization thereof would occur, thus requiring repolarization of the element. We have found that this additional step is not only necessary, but is economically feasible, in view of the much improved resistance to deterioration of the bond between the ceramic element and the orifice plate, especially in the aggressive medium of perfumes and insecticides, containing organic liquids, which can normally diffuse into epoxy resins and destroy them. In preparation of such a solder joint, a paste of appropriate flux material may be silk screened in the desired pattern, which when heated will distribute uniformly for application of the solder bead.

While shown in the previous Figures in the form of a concentric ceramic piezoelectric element surrounding an orifice plate or aperture, it is also conceived that the present invention is also suitable for use with a conventional piezoelectric element comprising an oscillator and a cantilever beam in contact with a diaphragm, nozzle, or orifice plate suitable for dispersion of liquid droplets or fog, as exemplified in FIG. 8.

As previously indicated, the invention itself is not limited to the preferred embodiments set forth heretofore, but is applicable to any configuration of piezoelectric element and dispensing means, such as a cantilever bar apparatus, as shown in FIG. 8. Here, a cantilever bar 20, having attachment means 19 for attachment to the body of an atomizer device, is in direct contact with a piezoelectric element 2, by means of solder joint attachment at attachment point 13. The bar is further in mechanical contact with the orifice plate 3, shown as a domed orifice plate, while any form may be used. The cantilever bar 20 is soldered to the orifice plate flanges 12, at attachment points 13, to provide a continuous and mechanically sound vibrational element for use in a piezoelectric atomizer.

As indicated above, it has been learned that specific combinations of improvements in the elements and methods of use of the dispenser described result in surprisingly improved results. Such results, however, are not limited to the preferred embodiment, but extend to piezoelectric atomizers in general. Specifically, we have learned that when atomizing fragrance oils and insecticide formulations, the bond mechanism between the orifice plate and the ceramic piezoelectric member frequently fails. In conventional atomizers, this mechanism frequently takes the form of a cantilever beam between the vibrating ceramic piezoelectric element and the orifice plate or membrane. Alternatively, the orifice plate may comprise a flange, which is mechanically joined to such transfer means as a metal amplification plate. Joining of such members is customarily accomplished by the use of adhesives, such as epoxy resins and cyanoacrylate adhesive formulations. However, such adhesive bonds are subject to degradation by aggressive media such as fragrance oils and organic solvent containing formulations, particularly under high frequency vibration, which promotes diffusion into the adhesive materials. To overcome this problem, it was found that use of a lead/tin solder eliminated such degradation. However, conventional wisdom dictated that such heat dependent joining means be avoided, since it resulted in depolarization of many ceramic piezoelectric elements. Thus, after soldering the members of the atomizer to be joined, it may be necessary to repolarize the ceramic piezoelectric element, dependent upon the specific properties of the piezoelectric material. Further, it was found that by use of solder to join the ceramic piezoelectric element directly to the metallic orifice plate, it was possible to eliminate the need for such vibration transfer means as the cantilever beam or an amplifying plate. For example, it was found that when dispensing a number of fragrances, epoxy bonded orifice plate to piezoelectric driver joints were rapidly deteriorated. Conversely, the same fragrances had negligible effect upon orifice plate to piezoelectric driver joints which were soldered, even after extensive periods of use.

Industrial Appicability

The atomization systems of the present invention can be used to automatically dispense such liquids as air fresheners, perfumes, insecticides, or other active liquids, to any given environment, over an extended period of time, with the advantage of uniformly dispensing equal amounts of liquid to the atmosphere over the life span of the battery which drives the dispenser. Further, the dispenser may be reused at will by means of refills and replacement batteries, so that the consumer may change the liquid being dispersed to the atmosphere as desired, with the added advantage that the amount of liquid being dispersed may be varied to adjust intensity or effectiveness to a desired level for personal preference, efficacy, or for room size.

While the present invention has been described with respect to what are at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

What is claimed is:

1. A method for joining members of an atomizer which are subject to vibration, said members comprising an orifice plate which is domed in a center region thereof and which has a surrounding flange, and a piezoelectric actuator element, said piezoelectric actuator element being formed as a ring and being positioned in concentric relationship to said plate, said method comprising:

metallizing the piezoelectric actuator at attachment points thereon, polarizing said piezoelectric actuator, using a lead/tin solder to solder said surrounding flange of said orifice plate to said piezoelectric actuator element at a temperature which causes depolarization thereof, and thereafter repolarizing the piezoelectric actuator element to overcome depolarization which occurs during soldering.

2. A method according to claim 1 and further including a step of applying a paste of flux material to a surface of said ceramic piezoelectric actuator element before soldering to cause solder to distribute evenly over said surface.

3. An atomizer comprising an orifice plate having apertures in a domed center region thereof and having a surrounding flange, and a ceramic piezoelectric element, said piezoelectric element being formed as a ring and positioned in a concentric relationship to said orifice plate, a capillary feed mechanism to supply a liquid to be dispensed to said orifice plate, and electronics to control dispensing of said liquid, a lead/tin solder joint between said flange of said orifice plate and attachment points on said ceramic piezoelectric element, said lead/tin solder joint being a joint which has been formed at a temperature which causes depolarization of said piezoelectric element, and said ceramic piezoelectric element being repolarized to overcome depolarization which occurred during formation of said solder joint.

* * * * *